(12) United States Patent
Fu et al.

(10) Patent No.: US 12,409,179 B2
(45) Date of Patent: Sep. 9, 2025

(54) PHARMACEUTICAL COMBINATION OF PIMOZIDE AND METHOTREXATE AND USE THEREOF

(71) Applicant: GENEROS BIOPHARMA LTD., Zhejiang (CN)

(72) Inventors: Xin-Yuan Fu, Hangzhou (CN); Chengchen Lufei, Hangzhou (CN); Xinyu Liu, Hangzhou (CN); Yi Zhou, Hangzhou (CN)

(73) Assignee: GENEROS BIOPHARMA LTD., Hangzhou (CN)

( * ) Notice: Subject to any disclaimer, the term of this patent is extended or adjusted under 35 U.S.C. 154(b) by 983 days.

(21) Appl. No.: 17/601,586

(22) PCT Filed: Apr. 3, 2020

(86) PCT No.: PCT/CN2020/083164
§ 371 (c)(1),
(2) Date: Oct. 5, 2021

(87) PCT Pub. No.: WO2020/207344
PCT Pub. Date: Oct. 15, 2020

(65) Prior Publication Data
US 2022/0211708 A1    Jul. 7, 2022

(30) Foreign Application Priority Data
Apr. 9, 2019 (CN) .......................... 201910281742.9

(51) Int. Cl.
A61K 31/519 (2006.01)
A61K 31/4468 (2006.01)
A61P 19/02 (2006.01)

(52) U.S. Cl.
CPC ........ *A61K 31/519* (2013.01); *A61K 31/4468* (2013.01); *A61P 19/02* (2018.01)

(58) Field of Classification Search
CPC .................................................. A61K 31/519
See application file for complete search history.

(56) References Cited

U.S. PATENT DOCUMENTS

| 2009/0298838 A1 | 12/2009 | Kamatani et al. |
| 2017/0219581 A1 | 8/2017 | Xin-Yuan et al. |

FOREIGN PATENT DOCUMENTS

| CN | 101854802 A | 10/2010 | |
| WO | WO-9962525 A1 | 12/1999 | |
| WO | WO-2018213027 A1 * | 11/2018 | ......... A61K 31/4406 |

OTHER PUBLICATIONS

Bujor et al. (Plos One | https://doi.org/10.1371/journal.pone.0221823 Sep. 6, 2019) retrieved on Sep. 19, 2024 (Year: 2019).*
Jul. 9, 2020 International Search Report issued in International Patent Application No. PCT/CN2020/083164.
Jul. 9, 2020 Written Opinion of the International Searching Authority issued in International Patent Application No. PCT/CN2020/083164.
Jia-Jie Chen et al. "The neuroleptic drug pimozide inhibits stem-like cell maintenance and tumorigenicity in hepatocellular carcinoma" Oncotraget vol. 8, No. 11, May 27, 2015 (May 27, 2015), pp. 17593-17609, in particular abstract.
Elizabeth Pigottl et al."1-Methyl-Tryptophan Synergizes with Methotrexate to Alleviate Arthritis in a Mouse Model of Arthritis" Autoimmunity vol. 47, No. 6, Sep. 30, 2014 (Sep. 30, 2014) pp. 409-418, in particular abstract.
Takatsugu Oike et al. "Stat3 as potential therapeutic target for rheumatoid arthritis" Scientific Reports, Sep. 8, 2017 (Sep. 8, 2017), see abstract.
Berge et al., *"Pharmaceutical Salts"*, Journal of Pharmaceutical Science 66: 1-19 (1977).
Clarke R. Issues in experimental design and endpoint analysis in the study of experimental cytotoxic agents in vivo in breast cancer and other models[J]. Breast Cancer Research & Treatment, 1997, 46(2-3): 255-278.
Mar. 30, 2023 Extended European search report issued in European Patent Application No. 207880311.
Apr. 11, 2023 Second Action issued in Chinese Patent Application No. 2020102602044.
K Visser, D van der Heijde. Optimai dosage and route of administration of methotrexate in rheumatoid arthritis: a systematic review of the literature[J]. Ann Rheum Dis 2009:68:1094-1099.
First Office Action dated Sep. 19, 2022 issued in Chinese Patent Application No. 2020102602044.
First Office Action dated Mar. 13, 2024 issued in Canadian Patent Application No. 3,136,230.
First Office Action dated Mar. 12, 2024 issued in Japanese Patent Application No. 2021-560721.
Wittich Doering, M.D. "Quinidine-Digoxin Interaction Pharmacokinetics, Underlying Mechanism and Clinical Implications", The New England Journal of Medicine, Aug. 23, 1979.
Harvey Sternbach, M.D. "The Serotonin Syndrome", Am J Psychiatry 148:6, Jun. 1991.

* cited by examiner

*Primary Examiner* — John S Kenyon
*Assistant Examiner* — Rehana Ismail
(74) *Attorney, Agent, or Firm* — Harness, Dickey & Pierce, P.L.C.

(57) ABSTRACT

Disclosed are a pharmaceutical combination of pimozide and methotrexate and use thereof. The pharmaceutical combination comprises methotrexate, a pharmaceutically acceptable salt thereof, a solvate thereof, or a solvate of pharmaceutically acceptable salt thereof, and pimozide, a pharmaceutically acceptable salt thereof, a solvate thereof, or a solvate of pharmaceutically acceptable salt thereof. The pharmaceutical combination can be used for the treatment of rheumatoid arthritis.

16 Claims, 6 Drawing Sheets

PHARMACEUTICAL COMBINATION OF PIMOZIDE AND METHOTREXATE AND USE THEREOF

CROSS-REFERENCE TO RELATED APPLICATIONS

This application is a U.S. National Phase Application under 35 U.S.C. 371 of International Application No. PCT/CN2020/083164, filed on Apr. 3, 2020, which claims the benefit of the China patent application CN201910281742.9 filed on Apr. 9, 2019. The entire disclosures of the above applications are incorporated herein by reference.

TECHNICAL FIELD

The present disclosure relates to a pharmaceutical combination of pimozide and methotrexate and use thereof.

BACKGROUND

Rheumatoid arthritis is a chronic systemic autoimmune disease characterized by synovial inflammation of joints. Its incidence is about 1% of the total population, mostly in the middle-aged and elderly, with more females than males, and there are approximately 11 million patients in China. The pathogenesis of rheumatoid arthritis is not completely understood in modern medicine, and there is no complete cure at present. Symmetrical multiple recurrent arthritis is the main manifestation, and the facet joints of hands and feet are most susceptible to involve. Early or acute onset joints are mostly red, swollen, hot, painful and dyskinesia. Late stage can lead to joint destruction, stiffness, deformity and loss of function, as well as osteoporosis and skeletal muscle atrophy. Throughout the whole disease progress, it can be accompanied by pathological changes, like fever, anemia, weight loss, vasculitis and subcutaneous nodules, and may involve multiple organs of the whole body, which is a disease with a high disability rate and significantly increases the mortality of patients.

At present, the first-line western medicine regimen is mainly immunosuppressive drugs, including methotrexate, sulfasalazine, leflunomide, chloroquine hydrate, and glucocorticoids, which relieve inflammatory symptoms by inhibiting the proliferation of immune cells. Methotrexate was originally used for cancer treatment, low-concentration methotrexate (10-25 milligrams per week) was used to treat rheumatoid arthritis since the 1960s and became the first-line therapy method in the 1980s, with therapeutic efficacy in 30% to 40% of patients. The main side effects are liver and gastrointestinal toxicity, and about 50% of patients stop taking the drug within a year because of side effects.

WO2018213027A1 reported that pimozide (referred to as Nib1 in the present disclosure) has significant therapeutic efficacy in animal models of arthritis, reducing disease severity by inhibiting STAT5 activity.

Content of the Present Invention

The technical problem to be solved in the present disclosure is to provide a pharmaceutical combination comprising methotrexate and pimozide and use thereof. The present inventors have found that the combined use of methotrexate and pimozide is more effective than methotrexate or pimozide alone in the treatment of rheumatoid arthritis.

In the first aspect, the present invention provides a pharmaceutical combination comprising:
a substance X, the substance X is methotrexate or a pharmaceutically acceptable salt thereof; and,
a substance Y, the substance Y is pimozide or a pharmaceutically acceptable salt thereof.

In the pharmaceutical combination, the substance X and the substance Y can be administered simultaneously or separately.

The "simultaneous administration" means, for example, that the substance X and the substance Y are contained in a separate pharmaceutical composition and administered simultaneously; alternatively, a "separate pharmaceutical composition comprising the substance X" and a "separate pharmaceutical composition comprising the substance Y" are administered simultaneously.

The "separately administration" means, for example, that a "separate pharmaceutical composition comprising the substance X" and a "separate pharmaceutical composition comprising the substance Y" are administered separately at different times, such as one of the "separate pharmaceutical composition comprising the substance X" and the "separate pharmaceutical composition comprising the substance Y" is administered first and the other is subsequently administered. The "separate administration" may be close in time or far away in time.

Whether administered simultaneously or separately, regimens of administration (including administration way, administration dose, administration interval, etc.) of the substance X and the substance Y, can be the same or different, which can be adjusted as needed by those skilled in the art to provide an optimal therapeutic effect.

In some embodiments, the substance X is administered by injection (e.g., intravenous injection, subcutaneous injection, or intramuscular injection).

In some embodiments, the substance X is orally administered.

In some embodiments, the substance Y is orally administered.

In some embodiments, the substance X is administered by injection (e.g., intravenous injection, subcutaneous injection, or intramuscular injection), and the substance Y is orally administered.

In some embodiments, the substance X is orally administered, and the substance Y is orally administered.

In another aspect, the present disclosure provides a pharmaceutical composition A comprising:
a substance X, the substance X is methotrexate or a pharmaceutically acceptable salt thereof;
a substance Y, the substance Y is pimozide or a pharmaceutically acceptable salt thereof; and,
a pharmaceutical excipient.

The pharmaceutical composition A is a separate pharmaceutical composition.

The pharmaceutical composition A can be made into various suitable dosage forms according to the way of administration, including dosage forms for gastrointestinal administration (e.g., oral dosage form) and non-gastrointestinal administration (e.g., injectable dosage form).

In some embodiments, the pharmaceutical composition A is presented in an oral dosage form.

In some embodiments, the pharmaceutical composition A is presented in an injectable dosage form.

In another aspect, the present disclosure also provides a pharmaceutical composition B comprising:
a first pharmaceutical composition comprising the substance X and the pharmaceutical excipient, the substance X is methotrexate or the pharmaceutically acceptable salt thereof; and, a second pharmaceutical composition comprising the substance Y and pharmaceutical excipient, the substance Y is pimozide or the pharmaceutically acceptable salt thereof.

The first pharmaceutical composition is a separate pharmaceutical composition, the second pharmaceutical composition is a separate pharmaceutical composition.

In some embodiments, the first pharmaceutical composition is presented in an injectable (e.g., intravenous injection, subcutaneous injection or intramuscular injection) dosage form.

In some embodiments, the first pharmaceutical composition is presented in an oral dosage form.

In some embodiments, the second pharmaceutical composition is presented in an oral dosage form.

In some embodiments, the first pharmaceutical composition is presented in an injectable dosage form, and the second pharmaceutical composition is presented in an oral dosage form.

In some embodiments, the first pharmaceutical composition is presented in an oral dosage form; and, the second pharmaceutical composition is presented in an oral dosage form.

In another aspect, the present disclosure provides a use of the pharmaceutical composition, the pharmaceutical composition A or the pharmaceutical composition B in the preparation of the medicament for the treatment of rheumatoid arthritis.

In another aspect, the present disclosure provides a use of the substance X in the preparation of the medicament for the treatment of rheumatoid arthritis, the substance X is methotrexate or the pharmaceutically acceptable salt thereof, wherein the substance X is combined with substance Y, and the substance Y is pimozide or the pharmaceutically acceptable salt thereof.

In another aspect, the present disclosure provides a use of the substance Yin the preparation of the medicament for the treatment of rheumatoid arthritis, the substance Y is pimozide or the pharmaceutically acceptable salt thereof, wherein the substance Y is combined with substance X, and the substance X is methotrexate or the pharmaceutically acceptable salt thereof.

In another aspect, the present disclosure provides a method for treating rheumatoid arthritis comprising administering a therapeutically effective amount of the pharmaceutical composition, the pharmaceutical composition A, or the pharmaceutical composition B to a subject in need thereof, such as human or mice.

Among the uses and treatment methods:

The administration regimens of the substance X and the substance Y (including administration way, administration dosage, administration interval, etc.) can be the same or different, which can be adjusted as needed by those skilled in the art to provide optimal therapeutic effect.

The substance X and the substance Y can be administered simultaneously or separately.

The substance X can be administered in any suitable way in the art, including oral administration, injection (e.g., intravenous injection, intramuscular injection, subcutaneous injection), etc.

In some embodiments, the substance X is administered by injection (e.g., intravenous injection, subcutaneous injection or intramuscular injection).

In some embodiments, the substance X is orally administered.

In some embodiments, the substance Y is orally administered.

In some embodiments, the substance X is administered by injection (e.g., intravenous injection, subcutaneous injection or intramuscular injection), and the substance Y is orally administered.

In some embodiments, the substance X is orally administered, and the substance Y is orally administered.

The substance X can be administered according to the body weight of the subject, and range of non-limiting examples can be 0.01 to 1 mg/kg (referring to the dosage for once), for example 0.01 mg/kg, 0.05 mg/kg, 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.7 mg/kg, 0.8 mg/kg, 0.9 mg/kg or 1 mg/kg. In some embodiments, the dosage of methotrexate is 0.05-0.5 mg/kg, e.g., 0.05 mg/kg, 0.10 mg/kg, or 0.5 mg/kg.

The dosage of the substance X can be administered at a frequency of QW (once a week), BIW (twice a week), or Q2W (once every two weeks). In some embodiments, the substance X is administered at a frequency of QW.

In some embodiments, the substance X is administered by injection (e.g., intravenous injection, subcutaneous injection, or intramuscular injection) with the above dosage, frequency.

In some embodiments, the substance X is orally administered with the above dosage, frequency.

In some embodiments, the substance X is administered by injection (e.g., intravenous injection, subcutaneous injection, or intramuscular injection) with 0.5 mg/kg, QW.

In some embodiments, the substance X is orally administered with 0.5 mg/kg, QW.

In some embodiments, the substance X is orally administered with 0.05 mg/kg, QW.

The substance X can also be administered with a fixed dosage to a subject, that is, a fixed or predetermined dosage is administered to the subject. Range of non-limiting examples of the fixed dosage (referring to the dosage for once) can be 0.01 to 50 mg, for example 0.01 mg, 0.1 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, or 50 mg.

The fixed dosage of the substance X can be administered at a frequency of QW (once a week), BIW (twice a week), or Q2W (every two weeks). In some embodiments, the substance X is administered at a QW frequency.

In some embodiments, the substance X is administered by injection (e.g., intravenous injection, subcutaneous injection, or intramuscular injection) with the fixed dosage, frequency.

In some embodiments, the substance X is orally administered with the fixed dosage, frequency.

The substance Y can be administered in any suitable way in the art, including oral administration, injection (e.g., intravenous injection, intramuscular injection, subcutaneous injection), etc.

In some embodiments, the substance Y is orally administered.

The substance Y can be administered according to the body weight of the subject, and range of non-limiting examples can be 0.01 to 10 mg/kg (referring to the dosage for once), e.g. 0.1 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 or 10 mg/kg. In some embodiments, the dosage of substance Y is 1-10 mg/kg, e.g., 1 mg/kg, 5 mg/kg, or 10 mg/kg.

The dosage of the substance Y can be administered at a frequency of QD (once a day), QOD (every other day), or QW (once a week).

In some embodiments, the substance Y is administered with the above dosage at a QOD frequency.

In some embodiments, the substance Y is orally administered with the above dosage, frequency.

In some embodiments, the substance Y is orally administered with 1 mg/kg, QOD.

In some embodiments, the substance Y is orally administered with 5 mg/kg, QOD.

In some embodiments, the substance Y is orally administered with 10 mg/kg, QOD.

The substance Y can also be administered with a fixed dosage to the subject, i.e. the fixed or predetermined dosage is administered to the subject. Range of non-limiting examples of the fixed dosage (referring to the dosage for once) can be 0.01 to 20 mg, e.g. 0.01 to 10 mg, for example, 0.01 mg, 0.1 mg, 0.5 mg, 1 mg, 2 mg, 3 mg, 4 mg, 5 mg, 6 mg, 7 mg, 8 mg, 9 mg, or 10 mg.

The fixed dosage of the substance Y can be administered at a frequency of QD (once a day), BID (twice a day), TID (three times a day), QOD (every other day), QW (once a week), BIW (twice a week), or Q2W (once every two weeks).

In some embodiments, the substance Y is administered with the fixed dosage at a QOD frequency.

In some embodiments, the substance Y is orally administered with the fixed dosage, frequency.

In some embodiments, the substance X is administered by injection (e.g., intravenous injection, subcutaneous injection, or intramuscular injection); and the substance Y is orally administered.

In some embodiments, the substance X is administered by injection (e.g., intravenous injection, subcutaneous injection, or intramuscular injection) with 0.05-0.5 mg/kg, QW, and the substance Y is administered orally with 1-10 mg/kg, QOD.

In some embodiments, the substance X is administered by injection (e.g., intravenous injection, subcutaneous injection, or intramuscular injection) with 0.5 mg/kg, QW, and the substance Y is administered orally with 10 mg/kg, QOD.

In some embodiments, the substance X is administered orally with 0.05-0.5 mg/kg, QW, and the substance Y is administered orally with 1-10 mg/kg, QOD.

In some embodiments, the substance X is administered orally with 0.5 mg/kg, QW, and the substance Y is administered orally with 5 mg/kg, QOD.

In some embodiments, the substance X is administered orally with 0.05 mg/kg, QW, and substance Y is administered orally with 1 mg/kg, QOD.

When the substance X and the substance Y are administered separately, they can be administered continuously according to their respective dosing cycles. The dosing cycle of the substance X and the substance Y can start at the same time or at different time. For example, the substance X and the substance Y can be administered on the same day, and continuously administered according to their respective dosing cycles; alternatively, the substance X can be administered on the second or third day or more after the substance Y being administered, and then both are administered continuously according to their respective dosing cycles.

In another aspect, the present disclosure provides a combination pharmaceutical kit comprising:

a first container containing the first pharmaceutical composition, and, a second container containing the second pharmaceutical composition.

In another aspect, the present disclosure provides a pharmaceutical combination comprising:

a substance M, the substance M is methotrexate, a pharmaceutically acceptable salt thereof, a solvate thereof, or, a solvate of pharmaceutically acceptable salt thereof; and, a substance N, the substance N is pimozide, a pharmaceutically acceptable salt thereof, a solvate thereof, or a solvate of pharmaceutically acceptable salt thereof.

In the pharmaceutical combination, the substance M and the substance N can be administered simultaneously or separately.

The "simultaneous administration" means, for example, that the substance M and the substance N are contained in a separate pharmaceutical composition and administered simultaneously, alternatively, a "separate pharmaceutical composition comprising the substance M" and a "separate pharmaceutical composition comprising the substance N" are administered simultaneously.

The "separately administration" means, for example, that a "separate pharmaceutical composition comprising the substance M" and a "separate pharmaceutical composition comprising the substance N" are administered separately at different time, such as one of the "separate pharmaceutical composition of the substance M" and the "separate pharmaceutical composition comprising the substance N" is administered first and the other is subsequently administered. The "separate administration" may be close in time or far away in time.

In the pharmaceutical composition, whether administered simultaneously or separately, regimens of administration (including administration way, administration dose, administration interval, etc.) of the substance M and the substance N, can be the same or different, which can be adjusted as needed by those skilled in the art to provide an optimal therapeutic effect.

In some embodiments, the substance M is administered by injection (e.g., intravenous injection, subcutaneous injection, or intramuscular injection).

In some embodiments, the substance M is orally administered.

In some embodiments, the substance N is orally administered.

In some embodiments, the substance M is administered by injection (e.g., intravenous injection, subcutaneous injection, or intramuscular injection), and the substance N is orally administered.

In some embodiments, the substance M is orally administered, and the substance N is orally administered.

In another aspect, the present disclosure provides a pharmaceutical composition C comprising:

a substance M, the substance M is methotrexate, a pharmaceutically acceptable salt thereof, a solvate thereof, or, a solvate of pharmaceutically acceptable salt thereof;

a substance N, the substance N is pimozide, a pharmaceutically acceptable salt thereof, a solvate thereof, or, a solvate of pharmaceutically acceptable salt thereof; and, a pharmaceutical excipient.

The pharmaceutical composition C can be made into various suitable dosage forms according to the way of administration, including dosage forms for gastrointestinal administration (e.g., oral dosage form) and non-gastrointestinal administration (e.g., injectable dosage form).

In some embodiments, the pharmaceutical composition C is presented in an oral dosage form.

In some embodiments, the pharmaceutical composition C is presented in an injectable dosage form.

In another aspect, the present disclosure also provides a pharmaceutical composition D comprising:

a third pharmaceutical composition comprising a substance M and a pharmaceutical excipient, the substance M is methotrexate, a pharmaceutically acceptable salt thereof, a solvate thereof, or, a solvate of pharmaceutically acceptable salt thereof; and a fourth pharmaceutical composition comprising a substance N and a pharmaceutical excipient, the substance N is pimozide, a pharmaceutically acceptable salt thereof, a solvate thereof, or, a solvate of pharmaceutically acceptable salt thereof.

In some embodiments, the third pharmaceutical composition is presented in an injectable (e.g., intravenous injection, subcutaneous injection or intramuscular injection) dosage form.

In some embodiments, the third pharmaceutical composition is presented in an oral dosage form.

In some embodiments, the fourth pharmaceutical composition is presented in an oral dosage form.

In some embodiments, the third pharmaceutical composition is presented in an injectable dosage form, and the fourth pharmaceutical composition is presented in an oral dosage form.

In some embodiments, the third pharmaceutical composition is presented in an oral dosage form, and, the fourth pharmaceutical composition is presented in an oral dosage form.

In another aspect, the present disclosure provides a use of the pharmaceutical composition, the pharmaceutical composition C or the pharmaceutical composition D in the preparation of the medicament for the treatment of rheumatoid arthritis.

In another aspect, the present disclosure provides a use of the substance M in the preparation of the medicament for the treatment of rheumatoid arthritis, the substance M is methotrexate, the pharmaceutically acceptable salt thereof, the solvate thereof, or, the solvate of pharmaceutically acceptable salt thereof, wherein the substance M is combined with substance N, and the substance N is pimozide, the pharmaceutically acceptable salt thereof, the solvate thereof, or, the solvate of pharmaceutically acceptable salt thereof.

In another aspect, the present disclosure provides a use of substance N in the preparation of the medicament for the treatment of rheumatoid arthritis, the substance N is pimozide, the pharmaceutically acceptable salt thereof, the solvate thereof, or, the solvate of pharmaceutically acceptable salt thereof, wherein the substance N is combined with substance M, and the substance M is methotrexate, the pharmaceutically acceptable salt thereof, the solvate thereof, or, the solvate of pharmaceutically acceptable salt thereof.

In another aspect, the present disclosure provides a method for treating rheumatoid arthritis comprising administering a therapeutically effective amount of the pharmaceutical composition, the pharmaceutical composition C, or the pharmaceutical composition D to a subject in need thereof, such as human or mice.

Among the uses and treatment methods:

The administration regimens of the substance M and the substance N (including administration way, administration dosage, administration interval, etc.) can be the same or different, which can be adjusted as needed by those skilled in the art to provide an optimal therapeutic effect.

The substance M and the substance N can be administered simultaneously or separately.

The substance M can be administered in any suitable way in the art, including oral administration, injection (e.g., intravenous injection, intramuscular injection, subcutaneous injection), etc.

In some embodiments, the substance M is administered by injection (e.g., intravenous injection, subcutaneous injection or intramuscular injection).

In some embodiments, the substance M is orally administered.

In some embodiments, the substance N is orally administered.

In some embodiments, the substance M is administered by injection (e.g., intravenous injection, subcutaneous injection or intramuscular injection), and the substance N is orally administered.

In some embodiments, the substance M is orally administered, and the substance N is orally administered.

The substance M can be administered according to the body weight of the subject, and range of non-limiting examples can be 0.01 to 1 mg/kg (referring to the dosage for once), e.g., 0.01 mg/kg, 0.05 mg/kg, 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.7 mg/kg, 0.8 mg/kg, 0.9 mg/kg or 1 mg/kg. In some embodiments, the dosage of the substance M is 0.05-0.5 mg/kg, e.g., 0.05 mg/kg, 0.10 mg/kg, or 0.5 mg/kg.

The dosage of the substance M can be administered at a frequency of QW (once a week), BIW (twice a week), or Q2W (once every two weeks). In some embodiments, the substance M is administered at a frequency of QW.

In some embodiments, the substance M is administered by injection (e.g., intravenous injection, subcutaneous injection, or intramuscular injection) with the dosage, frequency.

In some embodiments, the substance M is orally administered with the dosage, frequency.

In some embodiments, the substance M is administered by injection (e.g., intravenous injection, subcutaneous injection, or intramuscular injection) with 0.5 mg/kg, QW.

In some embodiments, the substance M is orally administered with 0.5 mg/kg, QW.

In some embodiments, the substance M is orally administered with 0.05 mg/kg, QW.

The substance M can also be administered with a fixed dosage to a subject, that is, the fixed or predetermined dosage is administered to the subject. Range of non-limiting examples of the fixed dosage (referring to the dosage for once) can be 0.01 to 50 mg, for example 0.01 mg, 0.1 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, or 50 mg.

The fixed dosage of the substance M can be administered at a frequency of QW (once a week), BIW (twice a week), or Q2W (every two weeks). In some embodiments, the substance M is administered at a QW frequency.

In some embodiments, the substance M is administered by injection (e.g., intravenous injection, subcutaneous injection, or intramuscular injection) with the fixed dosage, frequency.

In some embodiments, the substance M is orally administered with the fixed dosage, frequency.

The substance N can be administered in any suitable way in the art, including oral administration, injection (e.g., intravenous injection, intramuscular injection, subcutaneous injection), etc.

In some embodiments, the substance N is orally administered.

The substance N can be administered according to the body weight of the subject, and range of non-limiting examples can be 0.01 to 10 mg/kg (referring to the dosage for once), e.g. 0.1 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 or 10 mg/kg. In some embodiments, the dosage of the substance N is 1-10 mg/kg, e.g., 1 mg/kg, 5 mg/kg, or 10 mg/kg.

The dosage of the substance N can be administered at a frequency of QD (once a day), QOD (every other day), or QW (once a week).

In some embodiments, the substance N is administered with the dosage at a QOD frequency.

In some embodiments, the substance N is orally administered with the dosage, frequency.

In some embodiments, the substance N is orally administered with 1 mg/kg, QOD.

In some embodiments, the substance N is orally administered with 5 mg/kg, QOD.

In some embodiments, the substance N is orally administered with 10 mg/kg, QOD.

The substance N can also be administered with a fixed dosage to a subject, i.e. the fixed or predetermined dosage is administered to the subject. Range of non-limiting examples of the fixed dosage (referring to a dosage for once) can be 0.01 to 20 mg, e.g. 0.01 to 10 mg, for example, 0.01 mg, 0.1 mg, 0.5 mg, 1 mg, 2 mg, 3 mg, 4 mg, 5 mg, 6 mg, 7 mg, 8 mg, 9 mg, or 10 mg.

The fixed dosage of the substance N can be administered at a frequency of QD (once a day), BID (twice a day), TID (three times a day), QOD (every other day), QW (once a week), BIW (twice a week), or Q2W (once every two weeks).

In some embodiments, the substance N is administered with the fixed dosage at a QOD frequency.

In some embodiments, the substance N is orally administered with the fixed dosage, frequency.

In some embodiments, the substance M is administered by injection (e.g., intravenous injection, subcutaneous injection, or intramuscular injection), and the substance N is orally administered.

In some embodiments, the substance M is administered by injection (e.g., intravenous injection, subcutaneous injection, or intramuscular injection) with 0.05-0.5 mg/kg, QW; and the substance N is administered orally with 1-10 mg/kg, QOD.

In some embodiments, the substance M is administered by injection (e.g., intravenous injection, subcutaneous injection, or intramuscular injection) with 0.5 mg/kg, QW, and the substance N is administered orally with 10 mg/kg, QOD.

In some embodiments, the substance M is administered orally with 0.05-0.5 mg/kg, QW, and the substance N is administered orally with 1-10 mg/kg, QOD.

In some embodiments, the substance M is administered orally with 0.5 mg/kg, QW, and the substance N is administered orally with 5 mg/kg, QOD.

In some embodiments, the substance M is administered orally with 0.05 mg/kg, QW, and the substance N is administered orally with 1 mg/kg, QOD.

When the substance M and the substance N are administered separately, they can be administered continuously according to their respective dosing cycles. The dosing cycle of the substance M and the substance N can start at the same time or at different times. For example, the substance M and the substance N can be administered on the same day, and continuously administered according to their respective dosing cycles, alternatively, the substance M can be administered on the second or third day or more after the substance N being administered, and then both are administered continuously according to their respective dosing cycles.

In another aspect, the present disclosure provides a combination pharmaceutical kit comprising:
a third container containing the third pharmaceutical composition, and,
a fourth container containing the fourth pharmaceutical composition.

The term "treatment" as used herein refers to therapeutic therapy. When referring to a specific disease, treatment refers to: (1) alleviating one or more biological manifestations of a disease or disorder, (2) interfering with (a) one or more points in the biological cascade resulting in or causing disease, or (b) one or more biological manifestations of a disease, (3) improving one or more symptoms, effects or side effects related to a disease, or one or more symptoms, effects or side effects related to a disease or treatment thereof, or (4) alleviating the development of a disease or one or more biological manifestations of a disease.

The term "therapeutically effective amount" as used herein refers to an amount of a compound that is sufficient to effectively treat the disease or disorder described in the present disclosure when administered to a subject. The amount of the compound with "therapeutically effective amount" will vary according to the compound, the disorder and severity thereof, and the age of the subject to be treated, but can be adjusted by those skilled in the art as needed.

The term "container" as used herein refers to any container and closure suitable for storing, transporting, dispensing and/or handling medicaments.

The term "pharmaceutical composition" as used herein refers to a composition that comprises the specified active ingredients and can be prepared into the same dosage form.

The term "subject" as used herein refers to any animal that is about to or has been administrated of the compound or composition according to the embodiments of the present disclosure, mammals are preferred, and humans are most preferred. As used herein, the term "mammal" includes any mammal. Examples of mammals include, but are not limited to, cows, horses, sheep, pigs, cats, dogs, mice, rats, rabbits, guinea pigs, monkeys, humans, etc., with humans being the most preferred.

The term "pharmaceutical excipients" as used herein refers to excipients and additives used in the production of medicines and formulating prescriptions, and is all substances contained in pharmaceutical formulation except for active ingredients. Refer to the fourth part of the Chinese Pharmacopoeia (2015 edition), or, Handbook of Pharmaceutical Excipients (Raymond C Rowe, 2009 Sixth Edition).

The term "pharmaceutically acceptable" as used herein refers to acids or bases (used in the preparation of salts), solvents, excipients, etc. that are generally non-toxic, safe, and suitable for use by patients. The "patient" is preferably a mammal, more preferably a human.

The term "pharmaceutically acceptable salt" as used herein refers to a salt prepared from a compound with a relatively non-toxic, pharmaceutically acceptable acid or base. When the compound contains a relatively acidic functional group, the base addition salt can be obtained by contacting the neutral form of the compound with a sufficient amount of a pharmaceutically acceptable base in a pure solution or a suitable inert solvent. Pharmaceutically acceptable base addition salts include, but are not limited to: lithium salt, sodium salt, potassium salt, calcium salt, aluminum salt, magnesium salt, zinc salt, bismuth salt, ammonium salt, diethanolamine salt. When the compound contains a relatively basic functional group, the acid addition salt can be obtained by contacting the neutral form of the compound with a sufficient amount of a pharmaceutically acceptable acid in a pure solution or a suitable inert solvent. The pharmaceutically acceptable acids include inorganic acids, and the inorganic acids include, but are not limited to: hydrochloric acid, hydrobromic acid, hydroiodic acid, nitric acid, carbonic acid, hydrogen carbonate, phosphoric acid, monohydrogen phosphate, dihydrogen phosphate, phosphorous acid, sulfuric acid, hydrogen sulfate, etc. The pharmaceutically acceptable acids include organic acids, including but not limited to: acetic acid, propionic acid, oxalic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, salicylic acid, tartaric acid, methanesulfonic acid, isonicotinic acid, acid citric acid, oleic acid, tannic acid, pantothenic acid, hydrogen tartrate, ascorbic acid, gentisic acid, fumaric acid, gluconic acid, sugar acid, formic acid, ethanesulfonic acid, pamoic acid (ie 4,4'-methylene-bis(3-hydroxy-2-naphthoic acid)), amino acids (such as glutamic acid, arginine), etc. When the compound contains relatively acidic and relatively basic functional groups, it can be converted into base addition salt or acid addition salt. Refer to Berge et al., "Pharmaceutical Salts", Journal of Pharmaceutical Science 66: 1-19 (1977), or Handbook of Pharmaceutical Salts: Properties, Selection, and Use (P. Heinrich Stahl and Camille G. Wermuth, ed., Wiley-VCH, 2002).

The term "solvate" as used herein refers to a substance formed by combining the compound in the present disclosure with a stoichiometric or non-stoichiometric solvent. The solvent molecules in the solvate can exist in an ordered or non-ordered arrangement. The solvents include but are not limited to: water, methanol, ethanol and the like.

The term "pharmaceutically acceptable salt" and "solvate" in the term "solvate of pharmaceutically acceptable salt" as used herein, as described above, refers to a substance formed by the compound reacting with a relatively non-toxic and pharmaceutically acceptable acid or base and combining with a stoichiometric or non-stoichiometric solvent.

The "methotrexate", "pimozide", "pharmaceutically acceptable salt", "solvate" and "solvate of pharmaceutically acceptable salt" as used herein can exist in amorphous or crystalline form. The term "amorphous" refers to the disordered distribution of ions or molecules, that is, there is no periodic arrangement between ions and molecules. The term "crystal form" refers that the ions or molecules are arranged strictly and periodically in a three-dimensional space in a certain way, and have the regularity of periodic recurrence at a certain distance, due to the difference of the periodic arrangement, there are multiple crystal forms, that is, polymorphism.

If "methotrexate", "pimozide", "pharmaceutically acceptable salt", "solvate" and "solvate of pharmaceutically acceptable salt" as described herein have stereoisomers, they can exist in the form of a single stereoisomer or a mixture thereof (such as a racemate). The term "stereoisomer" refers to cis-trans isomers or optical isomers. These stereoisomers can be separated, purified and enriched by asymmetric synthesis methods or chiral separation methods (including but not limited to thin layer chromatography, rotation chromatography, column chromatography, gas chromatography, high pressure liquid chromatography, etc.), and can also be obtained by chiral resolution by bonding with other chiral compounds (chemical combination, etc.) or salting (physical combination, etc.). The term "single stereoisomer" refers that the mass content of a certain stereoisomer in the compound is not less than 95%. A typical single stereoisomer is an L-glutamic acid with a purity greater than 98.5%.

If "methotrexate", "pimozide", "pharmaceutically acceptable salt", "solvate" and "solvate of pharmaceutically acceptable salt" as described herein have tautomers, they can exist in the form of a single tautomer or a mixture thereof, preferably in the form of a relatively stable tautomer. Acetone and 1-propen-2-ol are typical tautomers with each other.

The atoms in the "methotrexate", "pimozide", "pharmaceutically acceptable salt", and "solvate" as described herein can exist in the form of their natural abundance or non-natural abundance. Taking the hydrogen atom as an example, the form of its natural abundance refers that about 99.85% whereof is protium and about 0.015% whereof is deuterium, the form of its unnatural abundance refers that about 95% whereof is deuterium. That is, one or more atoms of "methotrexate", "pimozide", "pharmaceutically acceptable salt", "solvate" and "solvate of pharmaceutically acceptable salt" can be atoms that exist in unnatural abundance. Alternatively, all atoms in "methotrexate", "pimozide", "pharmaceutically acceptable salt", "solvate" and "solvate of pharmaceutically acceptable salt" can also be atoms that exist in the form of natural abundance.

Unless otherwise specified, the singular forms of the terms "a" or "an" as used herein also includes the plural meaning.

The above preferred conditions of the present disclosure may be arbitrarily combined based on the general knowledge in the art to obtain the preferred embodiments of the present disclosure.

The reagents and raw materials used in the present disclosure are all commercially available.

The positive effects of the present disclosure are to provide a pharmaceutical composition comprising methotrexate and pimozide, in the treatment of rheumatoid arthritis, the combined use of methotrexate and pimozide is more effective compared with the single use of methotrexate or pimozide.

DETAILED DESCRIPTION OF THE PREFERRED EMBODIMENT

The following embodiments further illustrate the present disclosure, but the present disclosure is not limited thereto. In the following embodiments, the experimental methods without specific conditions are selected according to the conventional methods and conditions, or according to the product specification.

Embodiment 1: Evaluation of the Combined Therapeutic Effect of Oral Nib1 and Injection of Methotrexate in a Lewis Rat Adjuvant-Induced Arthritis Model Experimental Materials:
*Mycobacterium tuberculosis* H37 Ra was purchased from BD company, catalog number 231141;
Paraffin oil was purchased from Sinopharm Chemical Reagent Co., Ltd., catalog number 30139828;
Tofacitinib was purchased from Dalian Meilun Biological Company, China, and the catalog number is PBN2011586-01;
Methotrexate (MTX) was purchased from Shanghai Sangon Biotech Co., Ltd., catalog number A600612-005;
Pimozide (referred to as Nib1 in the present disclosure) was purchased from Sigma Corporation of the United States, the catalog number is P1793.

Experimental Method:
Preparation of Freund's complete adjuvant: heat-inactivated *Mycobacterium tuberculosis* was resuspended in paraffin oil (10 mg/mL, w/v), and sonicated in an ice bath for 30 minutes to form a stable suspension.

Lewis female rats aged 6-8 weeks were reared in SPF standard mouse houses, and after one week of adaptation, they were randomly divided into groups. The grouping and dosing regimens were shown in Table 1 below. Except for the normal control group, all animals in the other groups received subcutaneous inoculation of Freund's complete adjuvant, and 100 microliters were injected subcutaneously into the foot pad of the left hind limb (5 mg/kg dose). The normal control group received an injection of paraffin oil without *Mycobacterium tuberculosis*. The disease model animals received different treatment regimens, and the animal body weight was measured and the clinical symptoms of arthritis were evaluated (the scoring criteria was shown in Table 2) every three days until the end of the experiment. After the selected animals were sacrificed humanely, the joints were collected for pathological section analysis.

TABLE 1

Grouping and dosing regimens of Embodiment 1

| Group | Animal's number (n) | Group name | Therapeutic dose | Route of administration | Frequency |
| --- | --- | --- | --- | --- | --- |
| G1 | 5 | Normal | no | no | no |
| G2 | 10 | Vehicle | no | oral | Once every two days, four consecutive weeks |
| G3 | 10 | Tofacitinib | 5 mg/kg | oral | Once every two days, four consecutive weeks |
| G4 | 10 | Methotrexate | 0.5 mg/kg | Intraperitoneal injection | Once per week, four consecutive weeks |
| G5 | 10 | Nib1 | 10 mg/kg | oral | Once every two days, four consecutive weeks |
| G6 | 10 | Methotrexate and Nib1 | colspan="3" Methotrexate: Intraperitoneal injection of 0.5 mg/kg, once per week; Nib1: oral administration of 10 mg/kg, Once every two days, four consecutive weeks |

TABLE 2

Clinical scoring standard for the degree of arthritis

| Score | Clinical characterization |
| --- | --- |
| 0 | No swelling |
| 1 | Slightly congestion and swelling of one toe |
| 2 | Congestion and swelling of more than one toe, extending to the plantar |
| 3 | Inflammation and swelling of the entire plantar |
| 4 | Severe inflammation, swelling, or stiffness of the foot and plantar joints |

Experimental results of Embodiment 1 are as follows:

1. Results of Body Weight Change

Figure 1:
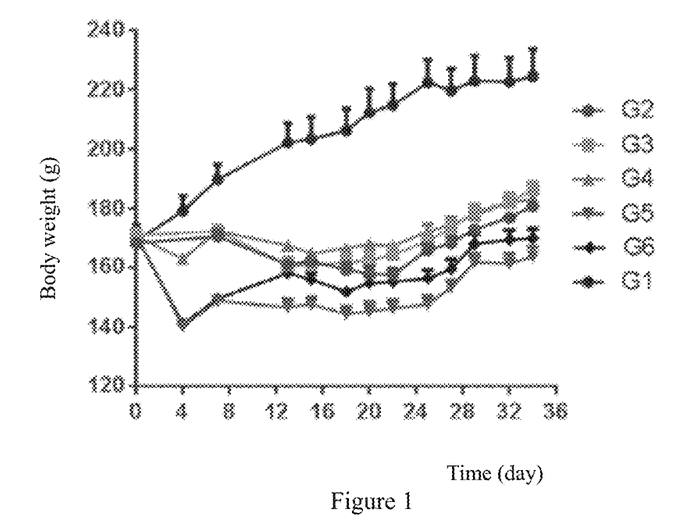
FIG. 1 is the results of changes in body weight of each group of animals in Embodiment 1 over time.

The results of the changes in body weight of each group of animals over time were shown in FIG. 1. The body weight of the disease model group was lower than the normal control, and the body weight of the Nib1 treatment group was lower than other groups, but there was no significant difference.

2. Clinical Scoring Results of the Degree of Arthritis

Figure 2:
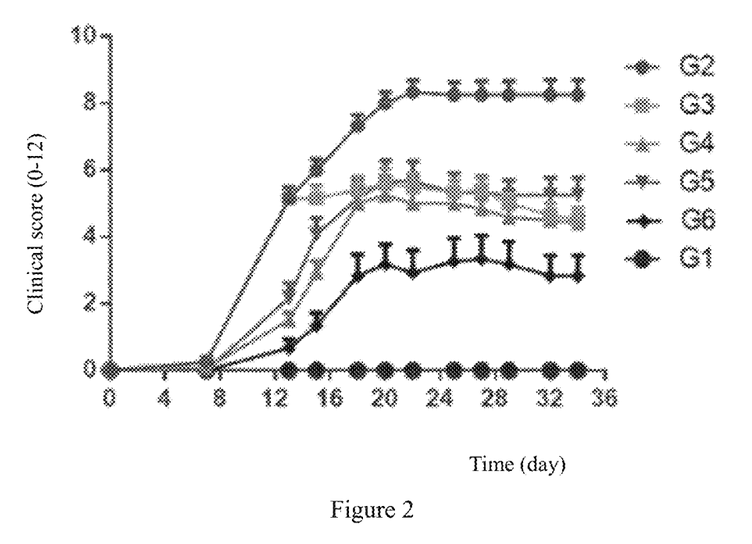
FIG. 2 is the results of changes of the sum of the scores of the quadrupedal joints of each group of animals in Embodiment 1 over time.

The results of changes of the sum of the scores of the quadrupedal joints of animals over time were shown in FIG. 2. It can be seen that the animal model was successfully established and the degree of morbidity was significant in the vehicle treatment group, the oral treatment effect of Nib1 alone was similar to that of the methotrexate and tofacitinib treatment group, and the combined Nib1 and methotrexate treatment group showed the best effect.

3. The Result of Changes in Paw Volume

Figure 3:
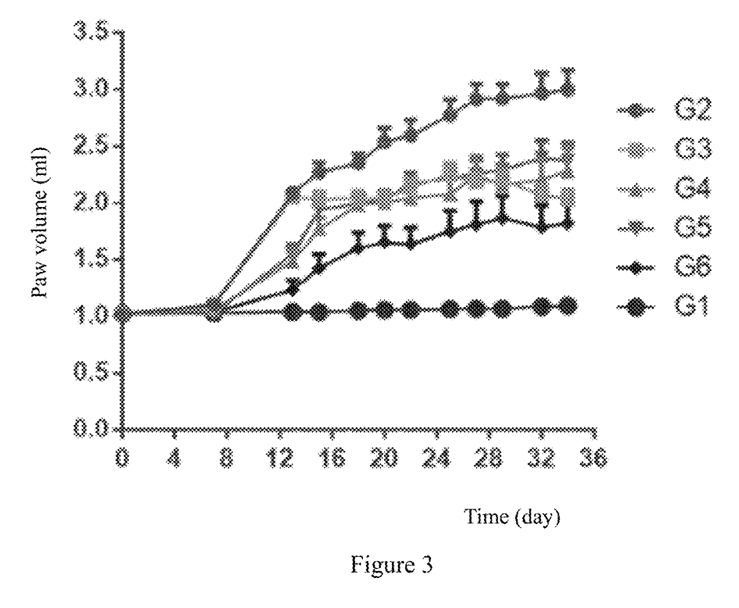
FIG. 3 is the results of changes in paw volume of each group of animals in Embodiment 1 over time.

The results of changes in the volume of the right hind foot over time were shown in FIG. 3, wherein the combined Nib1 and methotrexate group showed the best effect.

Figure 4:
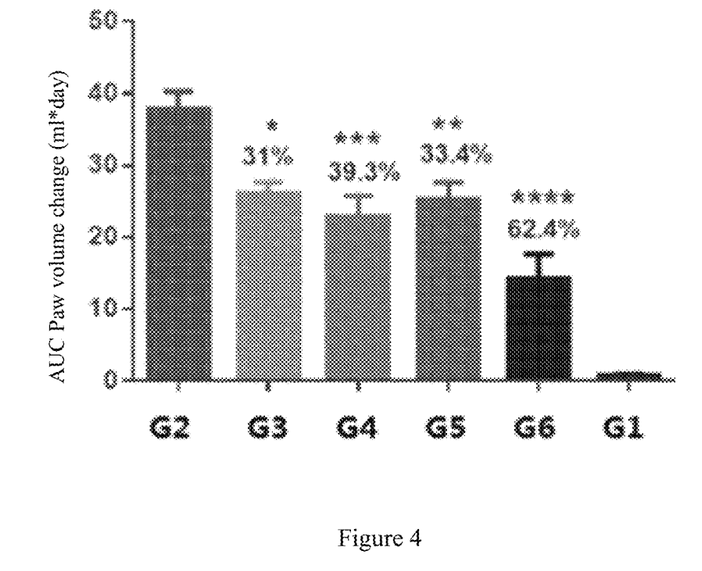
FIG. 4 is the analysis results of the area under the curve (AUC) of the paw volume over time in Embodiment 1.

4. The Analysis Results of Area Under the Curve (AUC) of the Changes in Paw Volume Over Time The changes in paw volume were analyzed by AUC, and the changes of therapeutic effects of the control vehicle group and other treatment groups were calculated separately, and there were significant differences, the results were shown in FIG. 4, each treatment group had significant differences compared to the control vehicle group, * P<0.05,  p<0.01, * p<0.001, **** p<0.0001, One-way ANOVA analysis.

The evaluation method of the combination effect refers to the literature, Clarke R. Issues in experimental design and endpoint analysis in the study of experimental cytotoxic agents in vivo in breast cancer and other models[J]. Breast Cancer Research & Treatment, 1997, 46(2-3): 255-278, the full text of which is incorporated herein by reference. The evaluation method is as follows:

Antagonism (AB/C)>(A/C)×(B/C)

Superposition (AB/C)=(A/C)×(B/C)

Synergy (AB/C)<(A/C)×(B/C)

wherein, A represents the effect of single drug 1, B represents the effect of single drug 2, AB represents the effect of combined use, and C represents the effect of the control group.

The synergy was calculated by the therapeutic effects of the single administration, the combined administration group achieved better results than the simple addition of the two therapies alone. The results were shown in Table 3.

TABLE 3

Synergy analysis of the combined administration group

|  | the single administration of methotrexate | the single administration of Nib1 | the combined administration of methotrexate and Nib1 |
| --- | --- | --- | --- |
| the therapeutic effects compared with vehicle group (paw volume x time AUC %) | 60.7% | 66.6% | 37.6% |

TABLE 3-continued

Synergy analysis of the combined administration group

|  | the single administration of methotrexate | the single administration of Nib1 | the combined administration of methotrexate and Nib1 |
| --- | --- | --- | --- |
| Theoretical value of synergy | — | — | 40.4% |

Experimental conclusion: Nib1 alone by oral administration (10 mg/kg, once every two days) had a significant therapeutic effect on the arthritis model, and was not inferior to tofacitinib (5 mg/kg, orally, once every two days), methotrexate (0.5 mg/kg, intraperitoneal injection, once a week). The combined use of oral Nib1 and methotrexate injection therapy had a synergistic effect (0.376<0.607×0.666=0.404).

Embodiment 2: The Therapeutic Effect of Oral Nib1 and Medium-Dose Methotrexate Therapy on Rat Adjuvant-Induced Arthritis Model Experimental Materials:

*Mycobacterium tuberculosis* H37 Ra was purchased from BD company, catalog number 231141;

Paraffin oil was purchased from Sinopharm Chemical Reagent Co., Ltd., catalog number 30139828;

Tofacitinib was purchased from Dalian Meilun Biological Company, China, and the catalog number is PBN2011586-01;

Methotrexate (MTX) was purchased from Shanghai Sangon Biotech Co., Ltd., catalog number A600612-005;

Pimozide (referred to as Nib1 in the present disclosure) was purchased from Sigma Corporation of the United States, the catalog number is P1793.

Experimental Method:

Preparation of Freund's complete adjuvant: heat-inactivated *Mycobacterium tuberculosis* was resuspended in paraffin oil (10 mg/mL, w/v), and sonicated in an ice bath for 30 minutes to form a stable suspension.

Lewis female rats aged 6-8 weeks were reared in SPF standard mouse houses, and after one week of adaptation, they were randomly divided into groups. The grouping and dosing regimens were shown in Table 4 below. Except for the normal control group, all animals in other groups received subcutaneous inoculation of Freund's complete adjuvant, and 100 microliters were injected subcutaneously into the foot pad of the left hind limb (5 mg/kg dose). One week later, the mice were again injected intracutaneously into the tail with the same dose of inactivated *Mycobacterium tuberculosis*. The normal control group received injection of paraffin oil without *Mycobacterium tuberculosis*. Oral administration was started on the day of the second immunization, the disease model animals received different treatment regimens, and the animal body weight was measured and the clinical symptoms of arthritis were evaluated (the scoring criteria was shown in Table 2) every three days until the end of the experiment. After the selected animals were sacrificed humanely, the joints were collected for pathological section analysis.

TABLE 4

Grouping and dosing regimens of Embodiment 2

| Group | Animal's number(n) | Group name | Administration regimen | | |
|---|---|---|---|---|---|
| | | | Therapeutic dose | Route of administration | Frequency |
| G1 | 3 | Normal | no | no | no |
| G2 | 8 | Vehicle | no | oral | Once even two days, four consecutive weeks |
| G3 | 8 | Tofacitinib 5 mpk | 5 mg/kg | oral | Once every two days, four consecutive weeks |
| G4 | 8 | MTX 0.5 mpk | 0.5 mg/kg | oral | Once every week, four consecutive weeks |
| G5 | 8 | Nib1 5 mpk | 5 mg/kg | oral | Once every two days, four consecutive weeks |
| G6 | 8 | Nib1 5 mpk + MTX 0.5 mpk | Nib1: 5 mg/kg MTX: 0.5 mg/kg | oral | Nib1, once every two days MTX, once per week four consecutive weeks |

1. Results of Weight Change

Figure 5:
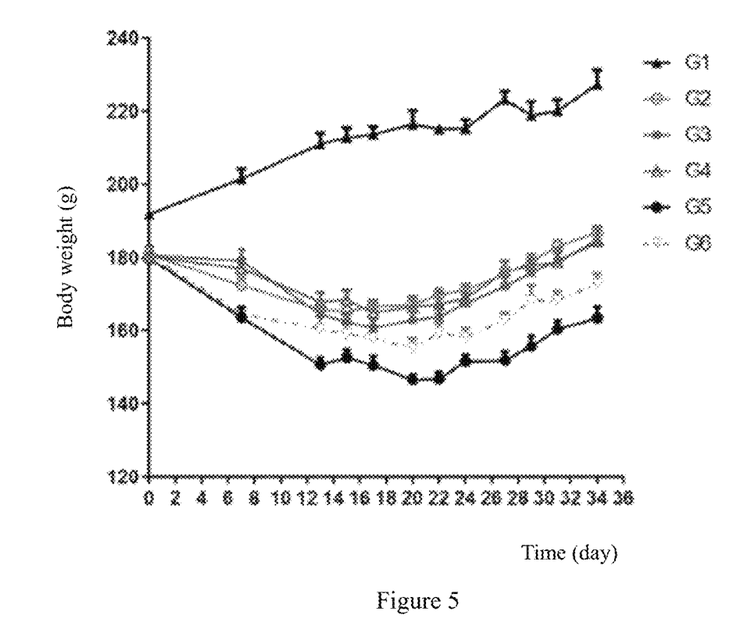
FIG. 5 is the results of changes in body weight of each group of animals in Embodiment 2 over time.

The results of the changes in body weight of each group of animals over time were shown in Table 5 and FIG. 5. The body weight of the disease treatment group was lower than that of the normal control group, while the weight of Nib1 5 mg/kg decreased significantly in the initial stage, and gradually recovered in the later stage. There was little difference in body weight between the treatment groups, and there was no significant difference compared with the control group.

TABLE 5

The weight change data of each group of animals in Embodiment 2 (unit: grams)

| Group | Time(day) | 0 | 7 | 13 | 15 | 17 | 20 | 22 | 24 | 27 | 29 | 31 | 34 |
|---|---|---|---|---|---|---|---|---|---|---|---|---|---|
| G1 | Average value | 191.93 | 201.60 | 211.07 | 212.83 | 213.73 | 216.47 | 215.20 | 215.37 | 223.23 | 218.87 | 220.17 | 227.40 |
| | variance | 0.49 | 4.85 | 5.27 | 4.61 | 3.56 | 6.64 | 2.18 | 4.14 | 3.98 | 6.74 | 5.42 | 6.82 |
| G2 | Average value | 180.95 | 172.38 | 165.73 | 165.15 | 166.68 | 167.05 | 169.84 | 171.08 | 175.50 | 178.91 | 183.23 | 186.84 |
| | variance | 5.48 | 6.36 | 5.18 | 3.62 | 3.86 | 4.60 | 4.42 | 4.74 | 4.83 | 5.02 | 4.39 | 4.67 |
| G3 | Average value | 180.74 | 179.19 | 164.45 | 162.41 | 160.70 | 162.90 | 163.78 | 167.38 | 172.06 | 175.80 | 179.24 | 184.08 |
| | variance | 7.13 | 8.88 | 4.38 | 6.22 | 6.76 | 9.66 | 7.73 | 7.45 | 7.75 | 9.88 | 10.23 | 10.57 |
| G4 | Average value | 180.41 | 177.01 | 167.89 | 168.50 | 164.89 | 166.48 | 167.25 | 168.85 | 176.03 | 177.90 | 178.74 | 184.88 |
| | variance | 7.47 | 6.83 | 7.17 | 7.18 | 9.87 | 7.48 | 8.94 | 10.80 | 8.73 | 8.31 | 7.68 | 10.23 |
| G5 | Average value | 179.78 | 163.63 | 150.66 | 152.64 | 150.56 | 146.58 | 146.80 | 151.84 | 155.73 | 160.36 | 163.41 | |
| | variance | 7.54 | 7.38 | 5.70 | 5.75 | 6.89 | 3.72 | 5.46 | 5.08 | 6.88 | 8.24 | 6.36 | 8.87 |
| G6 | Average value | 180.89 | 164.59 | 160.51 | 159.08 | 157.98 | 155.21 | 159.39 | 158.21 | 162.80 | 168.23 | 168.19 | 172.70 |
| | variance | 6.51 | 5.59 | 9.44 | 8.84 | 8.71 | 7.72 | 7.82 | 6.82 | 5.89 | 11.94 | 6.84 | 8.07 |

2. Clinical Scoring Results of Arthritis

Figure 6:
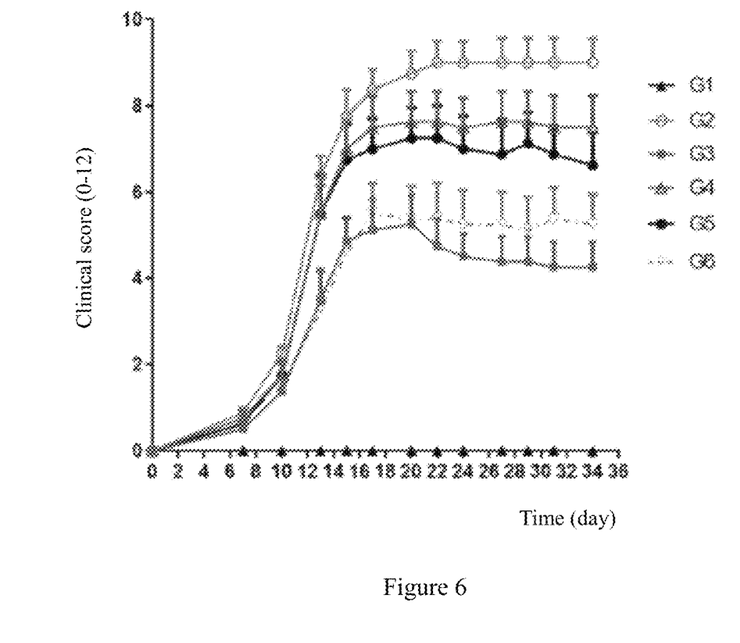
FIG. 6 is the results of changes of the sum of the scores of the quadrupedal joints of each group of animals in Embodiment 2 over time.

The results of the sum of the scores of the quadrupedal joints of each group of animals were shown in Table 6 and FIG. 6. The combined administration group (G6) showed a good therapeutic effect, which is similar to the tofacitinib treatment group.

TABLE 6

Clinical scoring data of arthritis of each group of animals in Embodiment 2

| Group | Time(day) | 0 | 7 | 13 | 15 | 17 | 20 | 22 | 24 | 27 | 29 | 31 | 34 |
|---|---|---|---|---|---|---|---|---|---|---|---|---|---|
| G1 | Average value | 0 | 0 | 0 | 0 | 0 | 0 | 0 | 0 | 0 | 0 | 0 | 0 |
| | variance | 0 | 0 | 0 | 0 | 0 | 0 | 0 | 0 | 0 | 0 | 0 | 0 |
| G2 | Average value | 0 | 0.88 | 2.25 | 6.38 | 7.75 | 8.38 | 8.75 | 9.00 | 9.00 | 9.00 | 9.00 | 9.00 |
| | variance | 0 | 0.35 | 0.46 | 1.30 | 1.75 | 1.30 | 1.49 | 1.41 | 1.41 | 1.60 | 1.60 | 1.60 |

TABLE 6-continued

Clinical scoring data of arthritis of each group of animals in Embodiment 2

| Group | Time(day) | 0 | 7 | 13 | 15 | 17 | 20 | 22 | 24 | 27 | 29 | 31 | 34 |
|---|---|---|---|---|---|---|---|---|---|---|---|---|---|
| G3 | Average value | 0 | 0.50 | 1.38 | 3.50 | 4.88 | 5.13 | 5.25 | 4.75 | 4.50 | 4.38 | 4.38 | 4.25 |
|    | variance      | 0 | 0.53 | 1.77 | 2.00 | 1.55 | 2.03 | 1.91 | 1.83 | 1.51 | 1.69 | 1.69 | 1.67 |
| G4 | Average value | 0 | 0.75 | 1.75 | 5.50 | 7.00 | 7.50 | 7.63 | 7.63 | 7.50 | 7.63 | 7.63 | 7.50 |
|    | variance      | 0 | 0.46 | 0.89 | 1.85 | 1.85 | 2.00 | 2.00 | 2.00 | 1.93 | 2.00 | 2.00 | 2.07 |
| G5 | Average value | 0 | 0.63 | 1.75 | 5.50 | 6.75 | 7.00 | 7.25 | 7.25 | 7.00 | 6.88 | 7.13 | 6.88 |
|    | variance      | 0 | 0.52 | 0.89 | 2.56 | 2.31 | 2.00 | 1.98 | 2.12 | 2.14 | 2.30 | 2.03 | 1.89 |
| G6 | Average value | 0 | 0.75 | 1.50 | 3.25 | 4.63 | 5.50 | 5.38 | 5.38 | 5.25 | 5.25 | 5.13 | 5.38 |
|    | variance      | 0 | 0.46 | 1.60 | 2.55 | 2.13 | 2.00 | 2.13 | 2.39 | 2.25 | 2.12 | 2.17 | 2.07 |

3. The Results of Changes in Paw Volume

Figure 7:
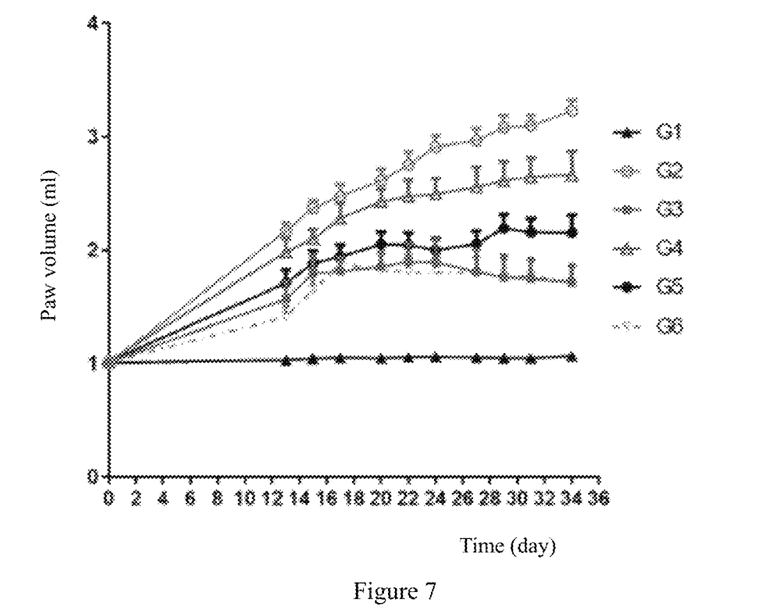
FIG. 7 is the results of changes in paw volume of each group of animals in Embodiment 2 over time.

The data of the volume of the right hind foot was shown in Table 7 and FIG. 7.

TABLE 7

The data of paw volume of each group of animals (unit: mL)

| Group | Time(day) | 0 | 7 | 13 | 15 | 17 | 20 | 22 | 24 | 27 | 29 | 31 | 34 |
|---|---|---|---|---|---|---|---|---|---|---|---|---|---|
| G1 | Average value | 1.01 | 1.03 | 1.04 | 1.05 | 1.04 | 1.05 | 1.06 | 1.05 | 1.05 | 1.04 | 1.06 | 1.01 |
|    | variance      | 0.02 | 0.02 | 0.01 | 0.01 | 0.02 | 0.02 | 0.02 | 0.02 | 0.02 | 0.01 | 0.02 | 0.02 |
| G2 | Average value | 1.01 | 2.17 | 2.37 | 2.48 | 2.62 | 2.75 | 2.91 | 2.97 | 3.08 | 3.10 | 3.23 | 1.01 |
|    | variance      | 0.01 | 0.22 | 0.19 | 0.29 | 0.28 | 0.32 | 0.28 | 0.30 | 0.31 | 0.27 | 0.26 | 0.01 |
| G3 | Average value | 1.01 | 1.57 | 1.80 | 1.81 | 1.85 | 1.90 | 1.89 | 1.81 | 1.76 | 1.74 | 1.71 | 1.01 |
|    | variance      | 0.02 | 0.43 | 0.44 | 0.37 | 0.36 | 0.48 | 0.58 | 0.57 | 0.56 | 0.51 | 0.42 | 0.02 |
| G4 | Average value | 1.02 | 1.98 | 2.10 | 2.28 | 2.43 | 2.48 | 2.50 | 2.56 | 2.62 | 2.65 | 2.66 | 1.02 |
|    | variance      | 0.03 | 0.34 | 0.24 | 0.36 | 0.32 | 0.41 | 0.38 | 0.50 | 0.47 | 0.47 | 0.60 | 0.03 |
| G5 | Average value | 1.02 | 1.71 | 1.88 | 1.94 | 2.05 | 2.05 | 2.00 | 2.06 | 2.20 | 2.16 | 2.16 | 1.02 |
|    | variance      | 0.02 | 0.34 | 0.32 | 0.30 | 0.31 | 0.31 | 0.29 | 0.33 | 0.34 | 0.34 | 0.44 | 0.02 |
| G6 | Average value | 1.01 | 1.41 | 1.64 | 1.87 | 1.82 | 1.80 | 1.80 | 1.80 | 1.78 | 1.77 | 1.72 | 1.01 |
|    | variance      | 0.02 | 0.28 | 0.35 | 0.39 | 0.42 | 0.42 | 0.42 | 0.43 | 0.42 | 0.40 | 0.42 | 0.02 |

Figure 8:
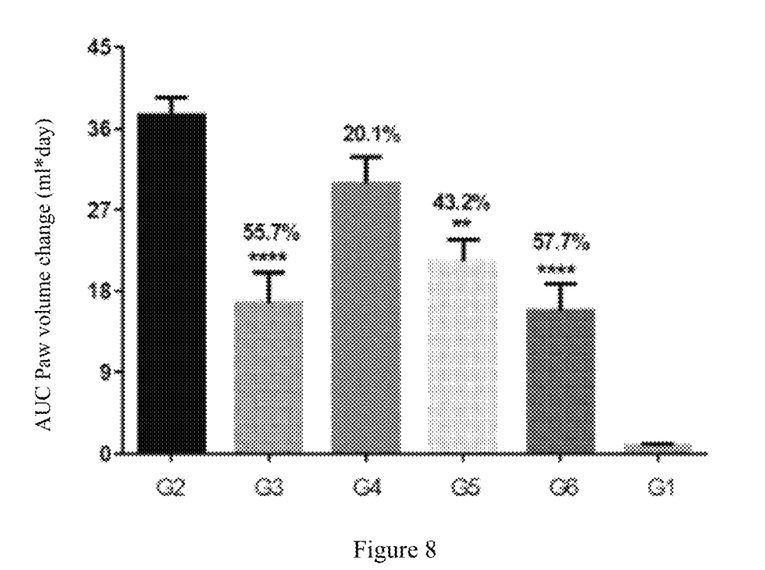
FIG. 8 is the analysis results of the area under the curve (AUC) of the paw volume over time in Embodiment 2.

4. The Analysis Results of Area Under the Curve (AUC) of the Change in Paw Volume Over Time The AUC analysis was performed on the change results of paw volume, the results were shown in FIG. 8. Each treatment group had significant difference compared to the control vehicle group, * P<0.05,  p<0.01, * p<0.001, **** p<0.0001, One-way ANOVA analysis.

The synergy was calculated based on the therapeutic effects of the single administration, the results were shown in Table 8. It can be seen that the combined medication group (G6) of Nib1(5 mg/kg) and methotrexate (0.5 mg/kg) showed synergistic effect, which achieved better effects than the simple addition of the two.

TABLE 8

Analysis of synergistic effect according to the AUC of changes in paw volume in Embodiment 2

| Group | Total area | Standard deviation | Relative to G2 percentage (%) | Theoretical value of synergy |
|---|---|---|---|---|
| G1 | 0.87  | 0.12 | —    | — |
| G2 | 37.5  | 1.42 | —    | — |
| G3 | 16.61 | 2.40 | 44.3 | — |
| G4 | 29.94 | 2.16 | 79.8 | — |
| G5 | 21.32 | 1.71 | 56.9 | — |
| G6 | 15.85 | 2.09 | 42.3 | 45.4 |

Embodiment 3: Evaluation of the Therapeutic Effect of Oral Nib1 and Methotrexate Therapy on Adjuvant-Induced Arthritis in Rats Experimental Materials:

*Mycobacterium tuberculosis* H37 Ra was purchased from BD company, catalog number 231141;

Paraffin oil was purchased from Sinopharm Chemical Reagent Co., Ltd., catalog number 30139828;

Tofacitinib was purchased from Dalian Meilun Biological Company, China, and the catalog number is PBN2011586-01;

Methotrexate (MTX) was purchased from Shanghai Sangon Biotech Co., Ltd., catalog number A600612-005;

Pimozide (referred to as Nib1 in the present disclosure) was purchased from Sigma Corporation of the United States, the catalog number is P1793.

Experimental Method:

Preparation of Freund's complete adjuvant: heat-inactivated *Mycobacterium tuberculosis* was resuspended in paraffin oil (10 mg/mL, w/v), and sonicated in an ice bath for 30 minutes to form a stable suspension.

Lewis female rats aged 6-8 weeks were reared in SPF standard mouse houses, and after one week of adaptation, they were randomly divided into groups. The grouping and dosing information was shown in Table 9. Except for the normal control group, all animals in the other groups received subcutaneous inoculation of Freund's complete adjuvant, and 100 microliters were injected subcutaneously into the foot pad of the left hind limb (5 mg/kg dose). One week later, the mice were again injected intracutaneously into the tail with the same dose of inactivated *Mycobacte-* rium tuberculosis. The normal control group received an injection of paraffin oil without Mycobacterium tuberculosis. Oral administration was started on the day of the second immunization, the disease model animals received different treatment regimens, and the animal body weight was measured and the clinical symptoms of arthritis were evaluated (the scoring criteria was shown in Table 2) every three days until the end of the experiment. After the selected animals were sacrificed humanely, the joints were collected for pathological section analysis.

TABLE 9

Groupine and dosing regimens of Embodiment 3

| Group | Animal's number(n) | Group name | Therapeutic dose | Route of administration | Frequency |
|---|---|---|---|---|---|
| G1 | 5 | Normal | no | no | no |
| G2 | 9 | Vehicle | no | oral | Once every day, four consecutive weeks |
| G3 | 9 | Tofacitinib 5 mpk | 5 mg/kg | oral | Once every day, four consecutive weeks |
| G4 | 9 | MTX 0.05 mpk | 0.05 mg/kg | oral | Once every week, four consecutive weeks |
| G5 | 9 | Nib1 1 mpk | 1 mg/kg | oral | Once every two days, four consecutive weeks |
| G6 | 9 | Nib1 1 mpk + MTX 0.05 mpk | Nib1: 1 mg/kg MTX: 0.05 mg/kg | oral | Nib1, once every two days MTX, once per week four consecutive weeks |

1. Results of Weight Change

Figure 9:
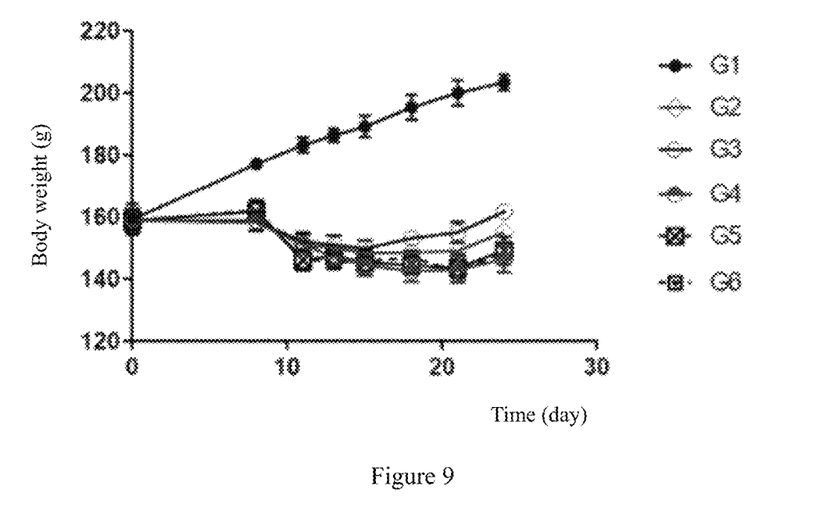
FIG. 9 is the results of changes in body weight of each group of animals in Embodiment 3 over time.

The results of the changes in body weight were shown in Table 10 and FIG. 9. There was no significant difference between the treatment groups.

TABLE 10

The weight change data of each group of animals in Embodiment 3 (unit: grams)

| Group | Time (day) | 0 | 8 | 11 | 13 | 15 | 18 | 21 | 24 |
|---|---|---|---|---|---|---|---|---|---|
| G1 | Average value | 159.20 | 177.20 | 183.20 | 186.40 | 189.20 | 195.40 | 200.00 | 203.40 |
|    | variance | 11.26 | 4.21 | 5.45 | 4.93 | 7.66 | 8.93 | 9.27 | 5.64 |
| G2 | Average value | 159.00 | 158.11 | 150.89 | 150.11 | 148.33 | 148.56 | 149.00 | 155.11 |
|    | variance | 6.46 | 6.01 | 6.49 | 6.53 | 5.41 | 4.98 | 3.91 | 5.13 |
| G3 | Average value | 158.78 | 158.44 | 152.00 | 151.00 | 149.78 | 153.11 | 155.00 | 161.67 |
|    | variance | 9.54 | 8.73 | 8.51 | 9.23 | 8.03 | 7.61 | 9.82 | 6.30 |
| G4 | Average value | 158.89 | 158.78 | 151.00 | 147.22 | 144.44 | 142.56 | 143.00 | 146.33 |
|    | variance | 11.01 | 9.95 | 9.64 | 7.69 | 8.55 | 10.32 | 12.58 | 12.79 |
| G5 | Average value | 158.78 | 161.78 | 146.00 | 147.56 | 145.22 | 144.56 | 143.56 | 149.22 |
|    | variance | 11.04 | 10.51 | 9.87 | 9.80 | 12.06 | 9.21 | 13.36 | 13.40 |
| G6 | Average value | 158.67 | 162.22 | 146.56 | 145.33 | 145.78 | 146.89 | 142.33 | 148.56 |
|    | variance | 11.99 | 8.81 | 8.79 | 6.89 | 6.83 | 6.81 | 6.22 | 6.77 |

2. Clinical Scoring Results of the Degree of Arthritis

Figure 10:
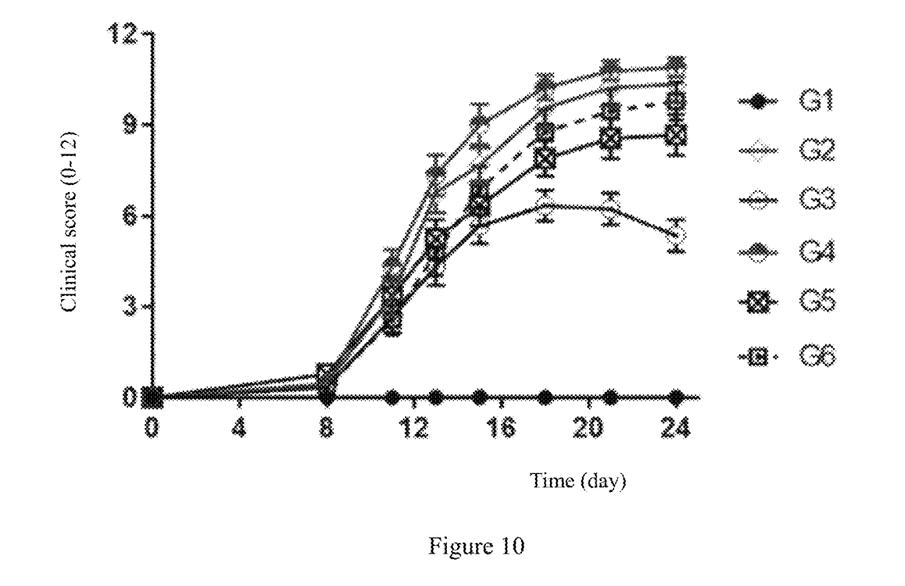
FIG. 10 is the results of changes of the sum of the scores of the quadrupedal joints of each group of animals in Embodiment 3 over time.

The results of the sum of the scores of the quadrupedal joints of each group of animals were shown in Table 11 and FIG. 10. The combined administration group showed a good therapeutic effect, which is similar to the tofacitinib treatment group.

TABLE 11

Clinical scoring data of arthritis of each group of animals in Embodiment 3

| Group | Time(day) | 0 | 8 | 11 | 13 | 15 | 18 | 21 | 24 |
|---|---|---|---|---|---|---|---|---|---|
| G1 | Average value | 0.00 | 0.00 | 0.00 | 0.00 | 0.00 | 0.00 | 0.00 | 0.00 |
|    | variance | 0.00 | 0.00 | 0.00 | 0.00 | 0.00 | 0.00 | 0.00 | 0.00 |
| G2 | Average value | 0.00 | 0.44 | 3.33 | 6.78 | 7.67 | 9.56 | 10.22 | 10.33 |
|    | variance | 0.00 | 0.73 | 1.94 | 2.05 | 1.73 | 2.01 | 1.86 | 1.80 |
| G3 | Average value | 0.00 | 0.33 | 2.67 | 4.33 | 5.67 | 6.33 | 6.22 | 5.33 |
|    | variance | 0.00 | 0.50 | 1.58 | 1.94 | 1.80 | 1.50 | 1.56 | 1.58 |
| G4 | Average value | 0.00 | 0.44 | 4.33 | 7.33 | 9.00 | 10.22 | 10.78 | 10.89 |
|    | variance | 0.00 | 0.53 | 1.58 | 2.00 | 2.00 | 1.20 | 0.97 | 0.93 |
| G5 | Average value | 0.00 | 0.78 | 3.33 | 5.22 | 6.33 | 7.89 | 8.56 | 8.67 |
|    | variance | 0.00 | 0.67 | 1.58 | 1.92 | 2.00 | 1.76 | 2.01 | 2.00 |
| G6 | Average value | 0.00 | 0.33 | 2.56 | 4.78 | 6.89 | 8.78 | 9.44 | 9.78 |
|    | variance | 0.00 | 0.50 | 1.51 | 2.28 | 2.26 | 2.17 | 2.13 | 1.86 |

3. The Results of Changes in Paw Volume

Figure 11:
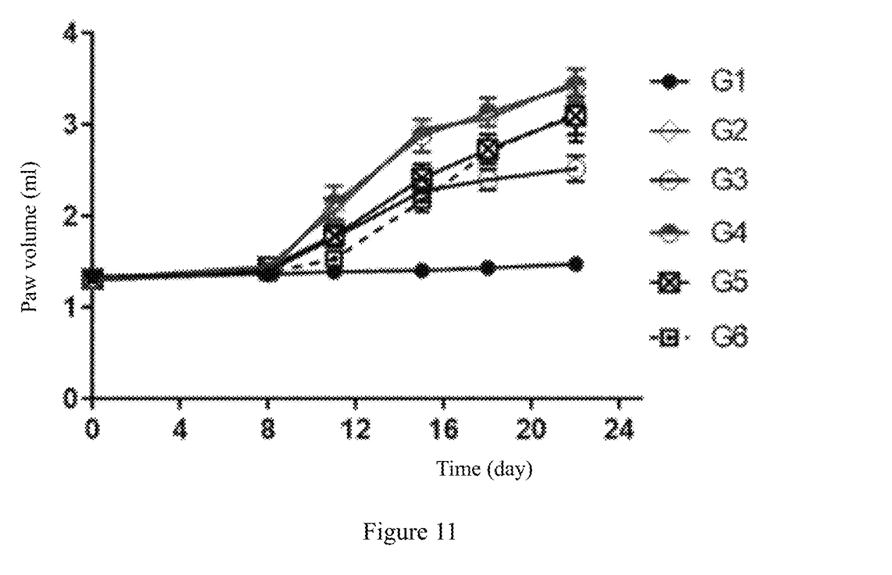
FIG. 11 is the results of changes in paw volume of each group of animals in Embodiment 3 over time.

The data of the volume of the right hind foot were shown in Table 12 and FIG. 11.

TABLE 12

The data of the volume of the right hind foot of each group of animals (unit: mL)

| Group | Time (day) | 0 | 8 | 11 | 15 | 18 | 22 |
|---|---|---|---|---|---|---|---|
| G1 | Average value | 1.34 | 1.36 | 1.39 | 1.40 | 1.43 | 1.47 |
|    | variance | 0.06 | 0.01 | 0.01 | 0.01 | 0.02 | 0.02 |
| G2 | Average value | 1.31 | 1.45 | 2.06 | 2.95 | 3.07 | 3.47 |
|    | variance | 0.03 | 0.24 | 0.39 | 0.33 | 0.27 | 0.30 |
| G3 | Average value | 1.31 | 1.40 | 1.76 | 2.27 | 2.40 | 2.52 |
|    | variance | 0.06 | 0.15 | 0.25 | 0.38 | 0.33 | 0.43 |
| G4 | Average value | 1.30 | 1.38 | 2.14 | 2.88 | 3.14 | 3.43 |
|    | variance | 0.06 | 0.10 | 0.55 | 0.54 | 0.46 | 0.53 |
| G5 | Average value | 1.31 | 1.44 | 1.79 | 2.41 | 2.73 | 3.10 |
|    | variance | 0.05 | 0.18 | 0.38 | 0.46 | 0.48 | 0.62 |
| G6 | Average value | 1.30 | 1.38 | 1.53 | 2.17 | 2.70 | 3.13 |
|    | variance | 0.03 | 0.05 | 0.23 | 0.38 | 0.40 | 0.96 |

4. The Analysis of Area Under the Curve (AUC) of the Change in Paw Volume

Figure 12:
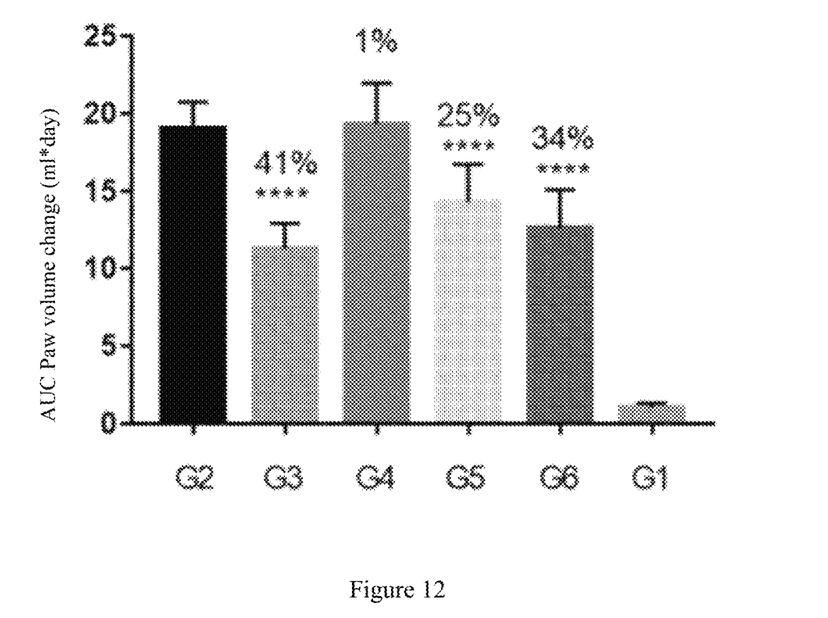
FIG. 12 is the analysis results of the area under the curve (AUC) of the paw volume over time in Embodiment 3.

AUC analysis was performed on the change curve of paw volume, compared to the vehicle group, the changes in therapeutic effects of each of the other treatment groups were calculated separately, and had significant differences (**** $p<0.0001$), as shown in FIG. 12.

According to the area under the paw volume curve, the synergistic effect was calculated according to the change ratio of ΔAUC relative to the vehicle group. The effect of using 0.05 mg/kg of methotrexate alone was not significant, but when combined with Nib1 (1 mg/kg, once every two days), ΔAUC exceeded the theoretical value of synergistic effect, showing a synergistic effect ($0.66<1.014\times0.749$)= 0.759), as shown in Table 13.

TABLE 13

Synergy analysis according to the AUC of changes in paw volume in Embodiment 3

| Group | Area under the curve AUC (ml*day) | Standard deviation | Relative to G2 percentage (%) | Theoretical value of synergy (%) |
|---|---|---|---|---|
| G1 | 1.03 | 0.27 | — | — |
| G2 | 19.05 | 1.68 | — | — |
| G3 | 11.27 | 1.66 | 59.2 | — |
| G4 | 19.31 | 2.63 | 101.4 | — |
| G5 | 14.26 | 2.45 | 74.9 | — |
| G6 | 12.57 | 2.50 | 66.0 | 75.9 |

Although the specific embodiments of the present disclosure are described above, those skilled in the art should understand that these are only examples, and various changes or modifications can be made to these embodiments without departing from the principle and essence of the present disclosure. Therefore, the protection scope of the present disclosure is defined by the appended claims

What is claimed is:

1. A pharmaceutical combination for the treatment of rheumatoid arthritis comprising:
    a substance M, the substance M is methotrexate, a pharmaceutically acceptable salt thereof, a solvate thereof, or, a solvate of pharmaceutically acceptable salt thereof; and,
    a substance N, the substance N is pimozide, a pharmaceutically acceptable salt thereof, a solvate thereof, or a solvate of pharmaceutically acceptable salt thereof.

2. The pharmaceutical combination as defined in claim 1, wherein, the substance M and the substance N are administered simultaneously or separately.

3. The pharmaceutical combination as defined in claim 1, wherein, the substance M is administered by injection or orally;
    and/or, the substance N is administered orally.

4. A pharmaceutical composition C for the treatment of rheumatoid arthritis comprising:
    a substance M, the substance M is methotrexate, a pharmaceutically acceptable salt thereof, a solvate thereof, or, a solvate of pharmaceutically acceptable salt thereof;
    a substance N, the substance N is pimozide, a pharmaceutically acceptable salt thereof, a solvate thereof, or, a solvate of pharmaceutically acceptable salt thereof; and,
    a pharmaceutical excipient.

5. The pharmaceutical composition C as defined in claim 4, wherein, the pharmaceutical composition C is presented in an oral dosage form or injectable dosage form.

6. A pharmaceutical composition D for the treatment of rheumatoid arthritis comprising:
- a pharmaceutical composition comprising a substance M and a pharmaceutical excipient, the substance M is methotrexate, a pharmaceutically acceptable salt thereof, a solvate thereof, or, a solvate of pharmaceutically acceptable salt thereof; and,
- a pharmaceutical composition comprising a substance N and a pharmaceutical excipient, the substance N is pimozide, a pharmaceutically acceptable salt thereof, a solvate thereof, or, a solvate of pharmaceutically acceptable salt thereof.

7. The pharmaceutical composition D as defined in claim 6, wherein, the pharmaceutical composition is presented in an injectable dosage form or oral dosage form.

8. A method of treating rheumatoid arthritis in a subject in need thereof, comprising administering the pharmaceutical combination as defined in claim 1 to the subject.

9. A method of treating rheumatoid arthritis in a subject in need thereof, comprising administering the substance M as defined in claim 1 to the subject, wherein the substance M is combined with the substance N, and the substance N is pimozide, the pharmaceutically acceptable salt thereof, the solvate thereof, or, the solvate of pharmaceutically acceptable salt thereof.

10. A method of treating rheumatoid arthritis in a subject in need thereof, comprising administering the substance N as defined in claim 1 to the subject, wherein the substance N is combined with the substance M, and the substance M is methotrexate, the pharmaceutically acceptable salt thereof, the solvate thereof, or, the solvate of pharmaceutically acceptable salt thereof.

11. The method as defined in claim 8, wherein the substance M and the substance N are administered simultaneously or separately.

12. The method as defined in claim 8, wherein the substance M is administered by injection or orally, and/or, the substance N is administered orally.

13. A method of treating rheumatoid arthritis in a subject in need thereof, comprising administering the pharmaceutical composition C as defined in claim 4 to the subject.

14. A method of treating rheumatoid arthritis in a subject in need thereof, comprising administering the pharmaceutical composition D as defined in claim 6 to the subject.

15. The method as defined in claim 13, wherein, the pharmaceutical composition C is presented in an oral dosage form or injectable dosage form.

16. The method as defined in claim 14, wherein, the pharmaceutical composition is presented in an injectable dosage form or oral dosage form.

* * * * *